United States Patent [19]

Stahl

[11] Patent Number: 5,224,651
[45] Date of Patent: Jul. 6, 1993

[54] APPARATUS FOR ATOMIZING AN ACTIVE SUBSTANCE

[76] Inventor: Werner Stahl, Saentisstrasse 52c, D-7770, Ueberlingen, Fed. Rep. of Germany

[21] Appl. No.: 942,422

[22] Filed: Sep. 9, 1992

[30] Foreign Application Priority Data

Sep. 10, 1991 [DE] Fed. Rep. of Germany ... 911204[U]

[51] Int. Cl.$^5$ .......................... B05B 7/02; B05B 1/34; B05B 17/06; A01C 1/08
[52] U.S. Cl. .................. 239/77; 239/102.2; 239/124
[58] Field of Search ............ 239/77, 78, 102.1, 102.2, 239/124, 14.2

[56] References Cited

U.S. PATENT DOCUMENTS

| | | | |
|---|---|---|---|
| 3,164,324 | 1/1965 | Bruinsma | 239/77 |
| 3,448,926 | 6/1969 | Knowles | 239/77 |
| 3,521,817 | 7/1970 | Curtis et al. | 239/77 |
| 3,674,208 | 7/1972 | Ballu | 239/77 |
| 3,851,823 | 12/1974 | Hori et al. | 239/102.2 |
| 3,904,119 | 9/1975 | Watkins | 239/405 |
| 3,904,347 | 9/1975 | Rokudo et al. | 431/1 |
| 3,966,123 | 6/1976 | Voorheis | 239/401 |
| 3,970,250 | 7/1976 | Drews | 239/102.2 |
| 4,251,031 | 2/1981 | Martin et al. | 239/102.2 |
| 4,337,896 | 7/1982 | Berger et al. | 239/102.2 |
| 4,509,683 | 4/1985 | Navarro | 239/77 |
| 4,609,145 | 9/1986 | Miller | 239/77 |
| 4,796,807 | 1/1989 | Bendig et al. | 239/102.2 |
| 4,815,661 | 3/1989 | Anthony | 239/102.2 |

FOREIGN PATENT DOCUMENTS

| | | |
|---|---|---|
| 0081261 | 6/1983 | European Pat. Off. . |
| 0075018 | 1/1987 | European Pat. Off. . |
| 2218709 | 10/1973 | Fed. Rep. of Germany . |
| 2604240 | 12/1976 | Fed. Rep. of Germany . |
| 1575041 | 6/1979 | Fed. Rep. of Germany . |
| 3706593 | 9/1987 | Fed. Rep. of Germany . |
| 3720938 | 1/1989 | Fed. Rep. of Germany . |
| 9105473.7 | 7/1991 | Fed. Rep. of Germany . |
| 4008845 | 9/1991 | Fed. Rep. of Germany . |
| 2285930 | 4/1976 | France . |
| 56-058555 | 5/1981 | Japan . |
| 600956 | 6/1978 | Switzerland . |

OTHER PUBLICATIONS

"Green House Sprayer" brochure (no date).
"Fontan Turbostar-E" brochure, Sep. 19, 1991.
"Turbosonic" brochure, 1990.
"Patent Abstracts of Japan" C-117, published Aug. 3, 1982, vol. 6, No. 143, with 57-65349.

Primary Examiner—Andres Kashnikow
Assistant Examiner—Karen B. Merritt
Attorney, Agent, or Firm—Foley & Lardner

[57] ABSTRACT

The invention relates to an apparatus for atomizing an active substance—in particular for pest control, crop protection, stock protection, disinfection, odor neutralization, or degerminating—having a casing surrounding an air-ducting outer shell. A fan is arranged in an inlet section of the air-ducting outer shell and an airducting inner shell is arranged downstream of the fan. Air-deflecting profiles extend between the air-ducting outer shell and the air-ducting inner shell. An atomizer arrangement is surrounded by the air-ducting inner shell, for atomizing active substance fed to it, which atomized active substance emerges from a downstream-directed active substance outlet opening in the air-ducting inner shell. A compressor is also located in the air-ducting inner shell. The compressor sucks in air through an annular inlet surrounding the active-substance outlet opening and through an annular channel formed between the compressor and the air-ducting inner shell into its inlet opening facing the fan, and feeds the air compressed by it through its outlet opening facing the active-substance outlet opening to a swirling stream nozzle surrounding the active-substance outlet opening.

15 Claims, 6 Drawing Sheets

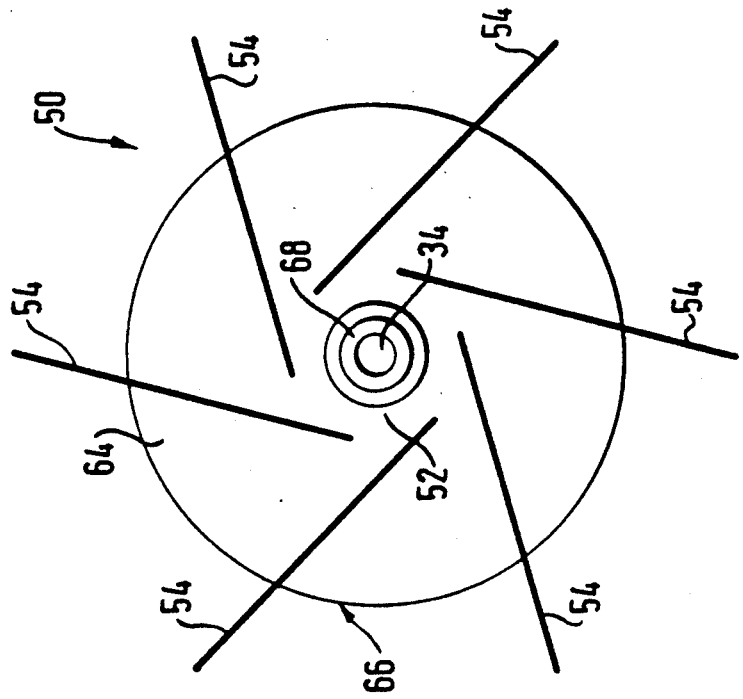
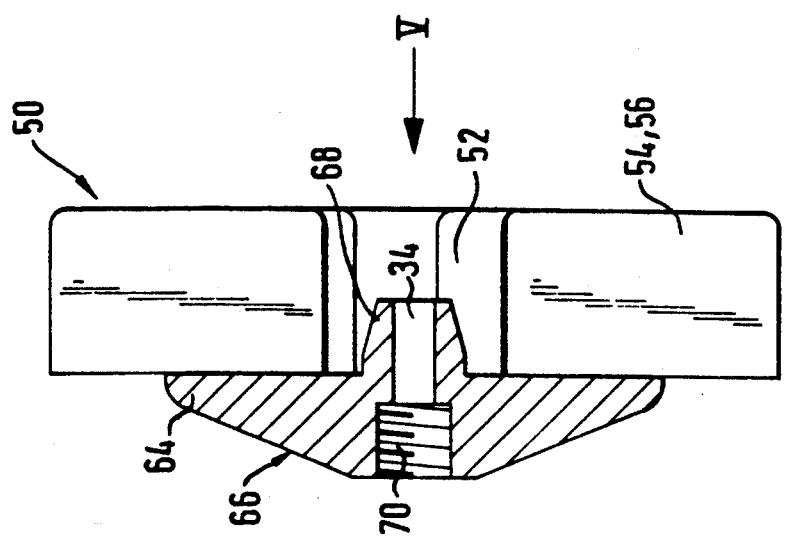

APPARATUS FOR ATOMIZING AN ACTIVE SUBSTANCE

FIELD OF THE INVENTION

The invention relates to an apparatus for atomizing an active substance—in particular for pest control, crop protection, stock protection, disinfection, odor neutralization or degerminating.

BACKGROUND OF THE INVENTION

In the case of an apparatus of this type known from the applicant's "turbosonic" brochure, there is an ultrasonic atomizer arrangement located in a casing surrounded by the air-ducting inner shell. Active substance not atomized by this ultrasonic atomizer arrangement collects in a sump of the casing and must therefore be sucked off by a suction removal device.

According to a "Green House Sprayer" brochure, a similar apparatus is known, which is provided with a compressor atomizer arrangement. Such an apparatus is voluminous, extremely heavy and must be fitted on wheels.

The same applies to a similar apparatus according to a "Fontan Turbostar-E" brochure of the Motan company.

SUMMARY OF THE INVENTION

One object of the invention is to specify an apparatus for atomizing an active substance—in particular for pest control, crop protection, stock protection, disinfection, odor neutralization or degerminating—having a casing surrounding an air-ducting outer shell, having a fan arranged in an inlet section of the air-ducting outer shell, having an air-ducting inner shell arranged downstream of the fan, having air-deflecting profiles extending between the air-ducting outer shell and the air-ducting inner shell and having an atomizer arrangement surrounded by the air-ducting inner shell for atomizing active substance fed to it, emerging from a downstream-directed active-substance outlet opening in the air-ducting inner shell.

To achieve this object, the apparatus is characterized by there being located in the air-ducting inner shell a compressor, which sucks in air through an annular inlet surrounding the active-substance outlet opening and through an annular channel formed between the compressor and the air-ducting inner shell into its inlet opening facing the fan, and feeds the air compressed by it through its outlet opening, facing the active-substance outlet opening, to a swirling stream nozzle surrounding the active-substance outlet opening.

In the case of the apparatus according to the invention, by virtue of the swirling stream nozzle, the compressor can be relatively small and lightweight. For example, a dust exhauster compressor which delivers 40 to 70 liters of air per second at a pressure of 120 to 140 mbar with a power consumption of 1000 to 1200 watts is sufficient. If the atomizer arrangement is a ultrasonic atomizer arrangement, the swirling stream nozzle prevents any dripping of the active substance when the active-substance atomization is stopped.

A swirling stream nozzle which is of a particularly simple construction and is effective for the purposes of the invention has a ring of deflecting surfaces which are inclined at equal angles with respect to radials, leave a central region free and the downstream edges of which are covered over radially on the outside by an annular surface. The airstream fed to the swirling stream nozzle is deflected radially inwards by the annular surface and is made by the deflecting surfaces to swirl with an axis coaxial with respect to the swirling stream nozzle. In this case, the deflecting surfaces are preferably plane or curved, in adaptation to the prevailing conditions.

In order to atomize the active substance within the swirling stream nozzle, there is preferably placed against the upstream edges of the swirling stream nozzle a body of an active-substance feed nozzle, which has an active-substance outlet nipple protruding into the central region of the swirling stream nozzle.

Preferably, there is coupled to the active-substance feed nozzle an ultrasonic generator, which sets the active-substance feed nozzle into axial oscillations, and the outlet end of the outlet nipple of the active-substance feed nozzle is surrounded by a radial flange. The active substance then flows out of the outlet nipple onto the downstream-side surface of the radial flange, forms waves there on account of the axial oscillations, and from the crests of the waves there are detached very fine droplets of active substance, for example having a droplet diameter spectrum of which the maximum is less than 50 $\mu$m, depending on the exciter frequency used, for example in the case of an exciter frequency of 120 kHz is around 12 $\mu$m. The swirling stream from the swirling stream nozzle in this case prevents not only any dripping of active substance from the active-substance feed nozzle when the ultrasonic generator or the supply of active substance is stopped, but also any overloading of the downstream-side surface of the annular flange by an excessively thick film of active substance. Independently of this, the combination of swirling-stream and ultrasonic atomization permits an increase in the airstream through the apparatus and consequently in the throwing range of the apparatus, a still finer atomization than with one of these types of atomization alone and a fine homogeneous atomizing of even relatively highly viscous active substances, active-substance suspensions and active-substance emulsions, which would not be possible with one of the types of atomization alone. Also, the downstream-side surface of the radial flange can be cleaned simply and effectively by means of the swirling stream nozzle.

An annular piezoelectric exciter fitted between a retaining flange of the active-substance feed nozzle and an active-substance inlet of the active-substance feed nozzle is particularly effective and of low weight.

In order that the piezoelectric exciter imparts a high oscillation amplitude on the radial flange at the outlet end of the outlet nipple, there is preferably placed against the side of the piezoelectric exciter facing the active-substance inlet of the active-substance feed nozzle an annular block which has a substantially greater mass than the part of the active-substance feed nozzle lying downstream of the retaining flange.

In order to prevent ambient contamination getting into the compressor, the above-mentioned annular inlet is preferably covered over by an annular filter.

In order to lead electrical lines to the compressor and, if appropriate, to the ultrasonic generator, preferably at least one of the above-mentioned air-deflecting profiles is hollow and receives these electrical lines.

In order to be able to feed optionally rinsing agent or active substance to the active-substance feed nozzle, feed lines are preferably led from a rinsing-agent tank and an active-substance tank in the casing and, if appropriate, from an outer third tank, to be connected to the apparatus, to a common feed line, containing a pump, to the active-substance feed nozzle.

If the active substance in the active-substance tank is a suspension, the active-substance tank is preferably assigned, that is, connected to, a circulating line, containing a second pump, by means of which the suspension is to be kept homogeneous in the active-substance tank.

In order to be able to allow the apparatus to work without further operation after switching on, there are preferably located in the feed lines solenoid valves which can be controlled by a program-control and a yes/no flow-meter in the common feed line. If, for example, the flow-meter establishes that active substance is no longer flowing, for instance because the active-substance tank is empty, it effects an automatic changeover to the rinsing-agent tank.

A particularly efficient construction is obtained if there are a pair of tanks respectively arranged in the space between the casing and the air-ducting outer shell at the top symmetrically with respect to the vertical longitudinal center plane of the casing and electrical installations are provided in this space at the bottom.

BRIEF DESCRIPTION OF THE DRAWINGS

The invention is described below by illustrative embodiments with reference to the attached drawings which are incorporated in and constitute a part of this specification, and, together with the description, serve to explain the principles of the invention.

FIG. 4 shows, enlarged, the region IV in FIG. 1 with a swirling stream nozzle;

FIG. 5 shows the swirling stream nozzle according to FIG. 4 from the viewing direction V in FIG. 4;

DETAILED DESCRIPTION OF THE PREFERRED EMBODIMENTS

Figure 1:
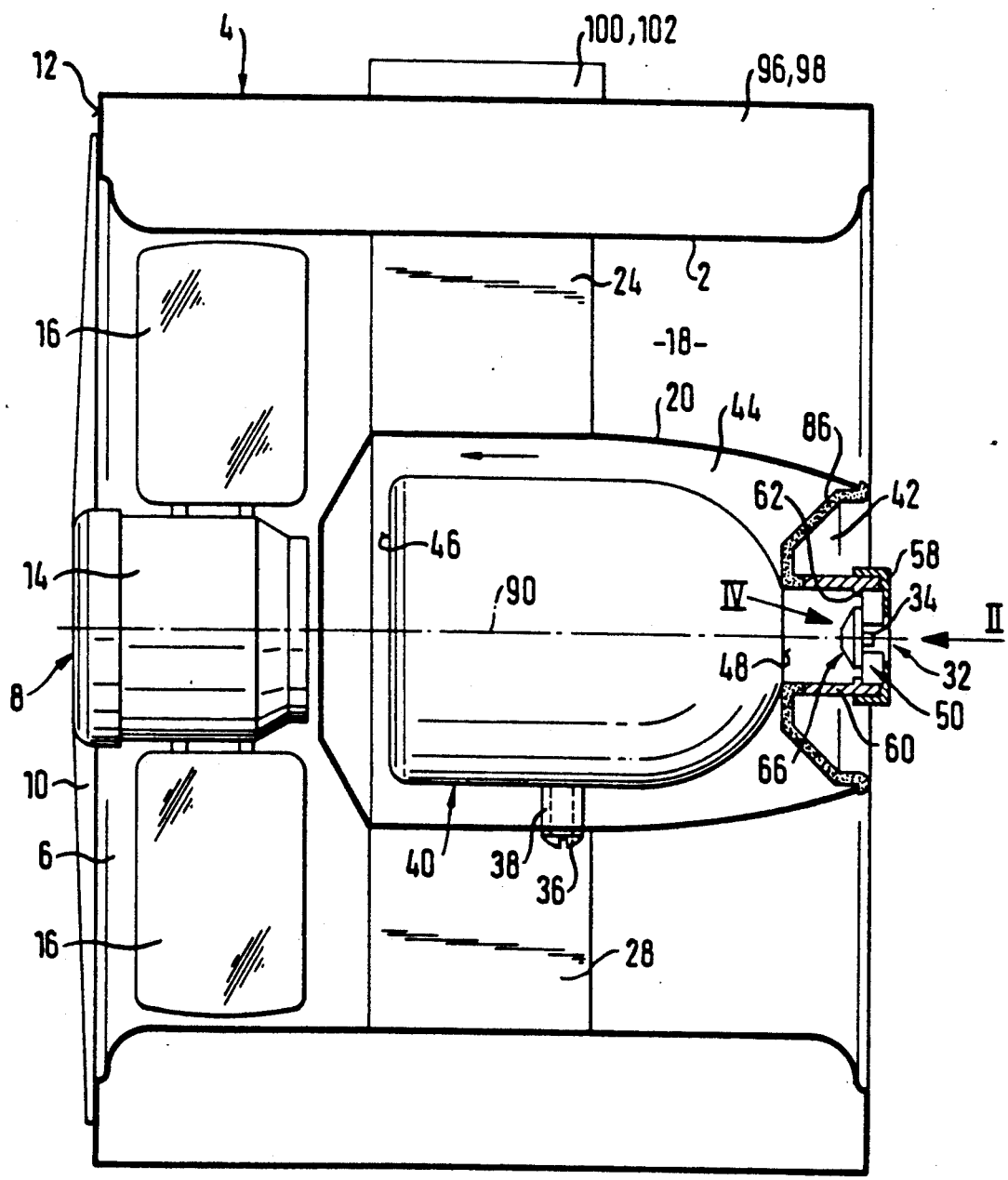
FIG. 1 shows an axial section through an embodiment of the apparatus.

As shown in FIG. 1, the apparatus according to the illustrative embodiment has a casing 4 surrounding an air-ducting outer shell 2. A fan 8 is arranged in an inlet section 6 of the air-ducting outer shell 2. A carrier of the fan 8 is a star 10, which serves also as protection and the ends of which are fastened to an end face 12 of the casing 4. The fan 8 has an inner stator (not visible) and a rotor 14, which carries at its circumference a ring of fan blades 16. Air is sucked in through the star 10 by the fan 8, conveyed into the space 18 surrounded by the air-ducting outer shell 2 and emerges from this space 18 axially from the casing 4. Arranged downstream of the fan 8 inside the air-ducting outer shell 2 is an air-ducting inner shell 20, which makes the space 18 into an annular space. Between the air-ducting outer shell 2 and the air-ducting inner shell 20 there extend air-deflecting profiles 22, 24, 26, 28, 30, which laminarize the airstream generated by the fan 8 and, moreover, keep the air-ducting inner shell 20 central in the air-ducting outer shell 2.

The downstream end of the air-ducting inner shell 20 surrounds an atomizer arrangement 32 for atomizing active substance fed to it, emerging atomized from a downstream-directed active-substance outlet opening 34 in the air-ducting inner shell 20.

Secured centrally in the air-ducting inner shell 20, by means of screws 36 which pass through spacer bushes 38, is a compressor 40, which sucks in air through an annular inlet 42 surrounding the active-substance outlet opening 34 and through an annular channel 44 formed between the compressor 40 and the air-ducting inner shell 20 into its inlet opening 46 facing the fan 8, and feeds the air compressed by it through its outlet opening 48, facing the active-substance outlet opening 34, to a swirling stream nozzle 50 surrounding the active-substance outlet opening 34.

From the swirling stream nozzle 50, atomized active substance emerges in the form of a jet, which is surrounded by a substantially laminar enclosing airstream from the space 18. By changing the speed of the fan 8, the range of the overall jet which emerges from the apparatus can be set.

The swirling stream nozzle 50 has a ring of deflecting surfaces 54 and 56, which are inclined at equal angles with respect to radials, leave a central region 52 free and the downstream edges of which are covered over radially on the outside by an annular surface on an annular cap 58, which serves for securing the swirling stream nozzle 50 on an outlet pipe connection 60 of the compressor 40. Located in the outlet pipe connection 60 there are abutment stops 62 for the swirling stream nozzle 50. In the embodiment according to FIG. 5 the deflecting surfaces 54 are plane, while in the embodiment according to FIG. 6 the deflecting surfaces 56 are curved.

As shown in FIG. 4, placed against the upstream edges of the swirling stream nozzle 50 is a body 64 of an active-substance feed nozzle 66, which has an active-substance outlet nipple 68 protruding into the central region 52 of the swirling stream nozzle 50 and, on the inlet side, an internal thread 70 for the connection of an active-substance feed line.

In the embodiment according to FIG. 7, there is coupled to the active-substance feed nozzle 66 an ultrasonic generator 72, which sets the active-substance feed nozzle 66 into axial oscillations. The outlet end of its active-substance outlet nipple 68 is surrounded by a radial flange 74, which has the significance mentioned above. The ultrasonic generator 72 and radial flange 74 comprise an ultrasonic atomizer.

A piezoelectric exciter, having two rings 80, 82, is fitted as ultrasonic generator 72 between a retaining flange 76 of the active-substance feed nozzle 66 and an active-substance inlet pipe connection 78 of the active-substance feed nozzle 66. Placed against the side of the piezoelectric exciter 80, 82 facing the active-substance inlet pipe connection 78 is an annular block 84 which has a substantially greater mass than the part of the active-substance feed nozzle 66 lying downstream of the retaining flange 76. The excitation frequency of the piezoelectric exciter 80, 82 is set to a resonant frequency of the active-substance feed nozzle 66 and of the masses associated with it. The retaining flange 76 is screwed by means of a union nut 77 onto the body 64, interposing a flexible ring 79. Since the body 64 is fastened on the casing 4 by means of the deflecting surfaces 54 or 56, the outlet pipe connection 60, the compressor 40, the screws 36, the spacer bushes 38, the air-ducting inner shell 20, the air-deflecting profiles 22, 24, 26, 28, 30 and the air-ducting outer shell 2, it is fixed to the casing and the ultrasonic generator 72 is therefore flexibly coupled to the casing 4, which improves the oscillating capability of the active-substance feed nozzle 66. In order that no active substance gets onto the flexible ring 79, an annular-conical shoulder 81 on the body 64 surrounds the radial flange 74 with a small spacing.

As can be seen from FIG. 1, the annular inlet 42 is covered over by an annular filter 86.

Figure 3:
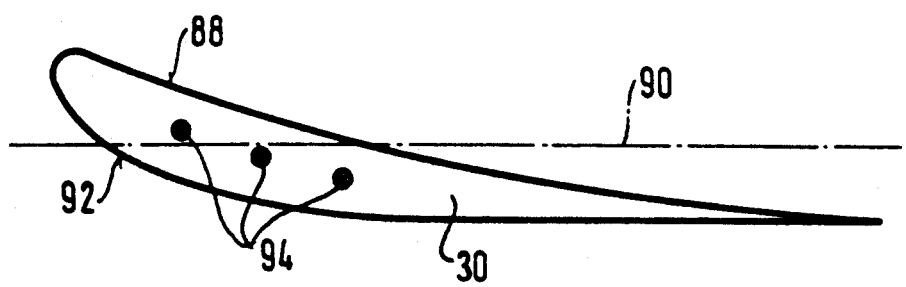
FIG. 3 shows a section along the line III—III in FIG.2.
Figure 6:
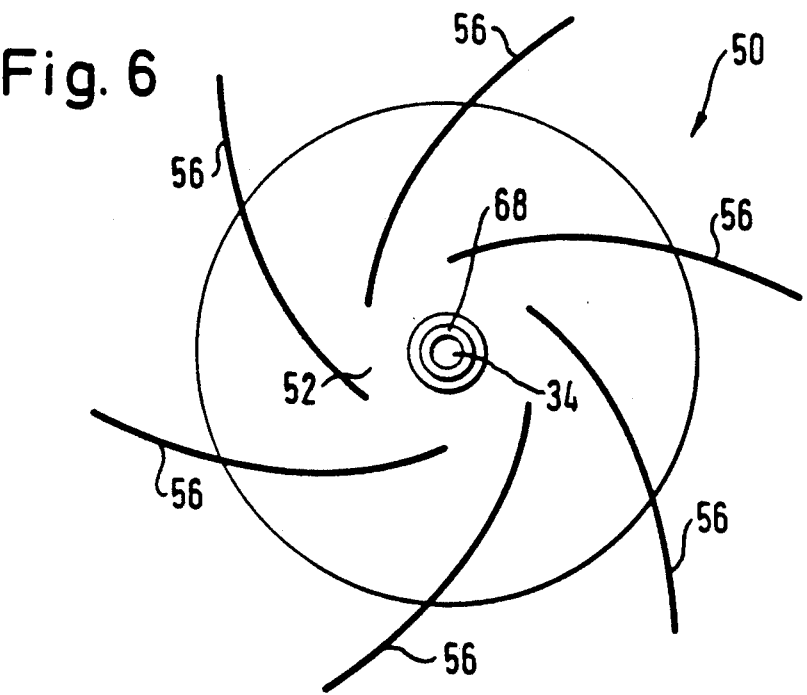
FIG. 6 shows, in a view corresponding to FIG. 5, a differently designed swirling stream nozzle.
Figure 7:
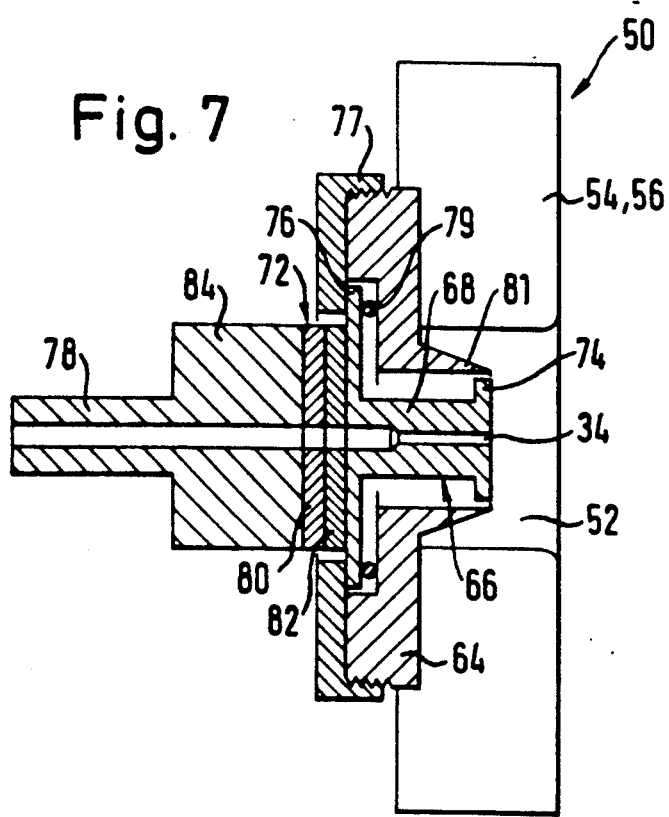
FIG. 7 shows, in a view corresponding to FIG. 4, a swirling stream nozzle united with an ultrasonic generator.

As can be seen from FIG. 3, in this illustrative embodiment the deflecting profile 30 is of a hollow and streamlined design. Its inner surface 88 has a form which corresponds to the non-hollow air-deflecting profiles 22, 24, 26, 28 and, in radial view, intersects the common axis 90 of the fan 8 and of the compressor 40. Its outer surface 92 is more strongly curved. Electrical lines 94 are laid in the air-deflecting profile 30.

Figure 8:
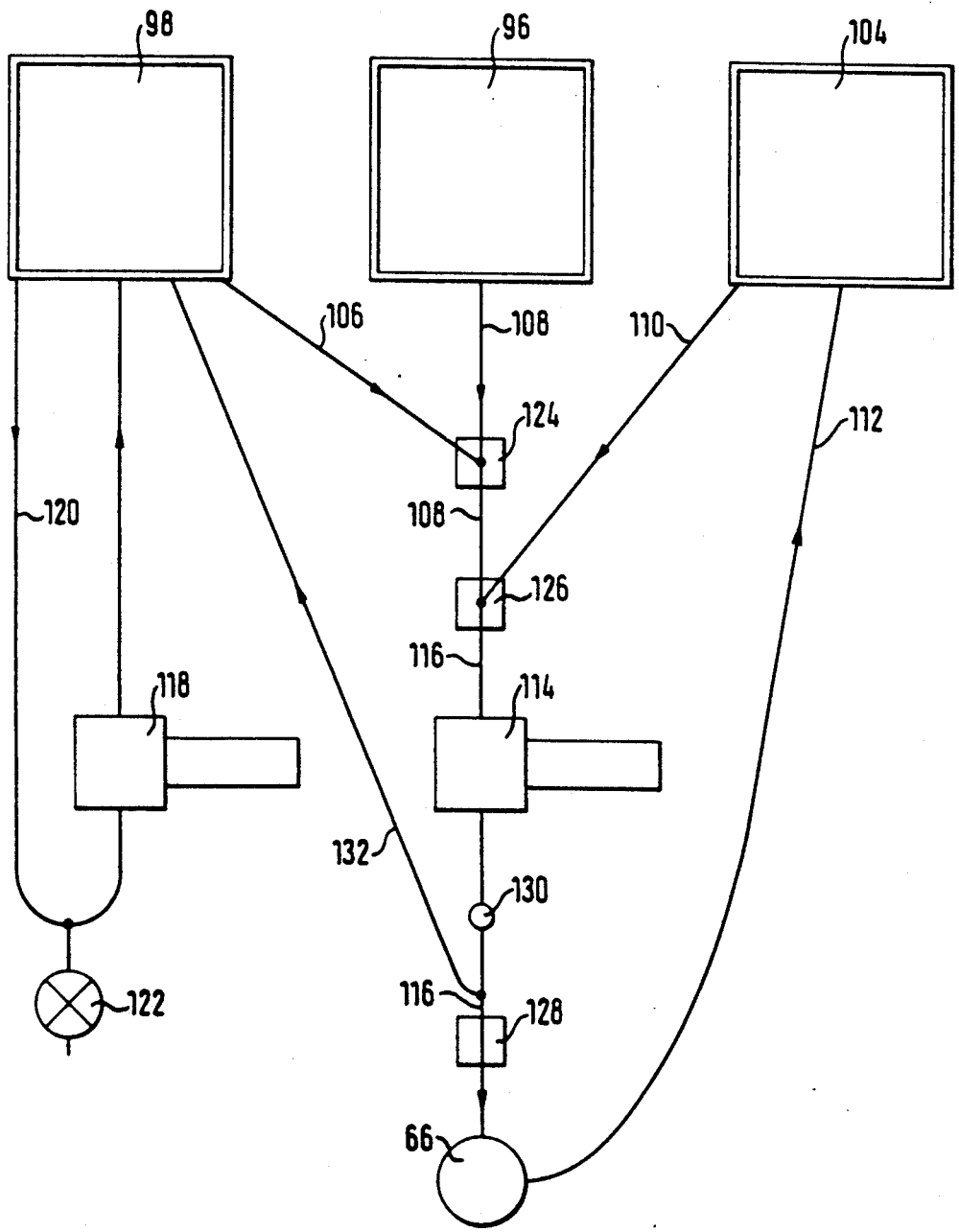
FIG. 8 shows a schematic diagram of the apparatus.

As shown in FIG. 8, feed lines 106, 108, 110 are led from a rinsing-agent tank 96 and an active-substance tank 98 in the casing 4, which have filler necks 100, 102 protruding upward out of the casing 4, and, if appropriate, from an outer third tank 104, to be connected (see FIG. 8), to a common feed line 116, containing a pump 114, to the active-substance feed nozzle 66. The active-substance tank 98 is connected to a second pump 118 in a circulating line 120, which has a drain tap 122. The line 106 is connected to the line 108 via a three-way/two-position valve 124, the line 110 is connected to the line 108 via a three-way/two-position valve 126. Both of these valves 124, 126 lie upstream of the pump 114. Between the pump 114 and the active-substance feed nozzle 66 there lies a two-way/two-position shut-off valve 128 in the common feed line 116. Between the valve 128 and the pump 114 there lies a yes/no flowmeter 130 in the common feed line 116. The valves 124, 126, 128 are designed as solenoid valves and can be controlled in the way described above. Between the yes/no flowmeter 130 and the valve 128, there is branched off from the common feed line 116 a return line 132 for returning active substance into the active-substance tank 98. From the active-substance feed nozzle 66 there leads a line 112 to the outer tank 104, in order to put this tank 104 under pressure.

Figure 2:
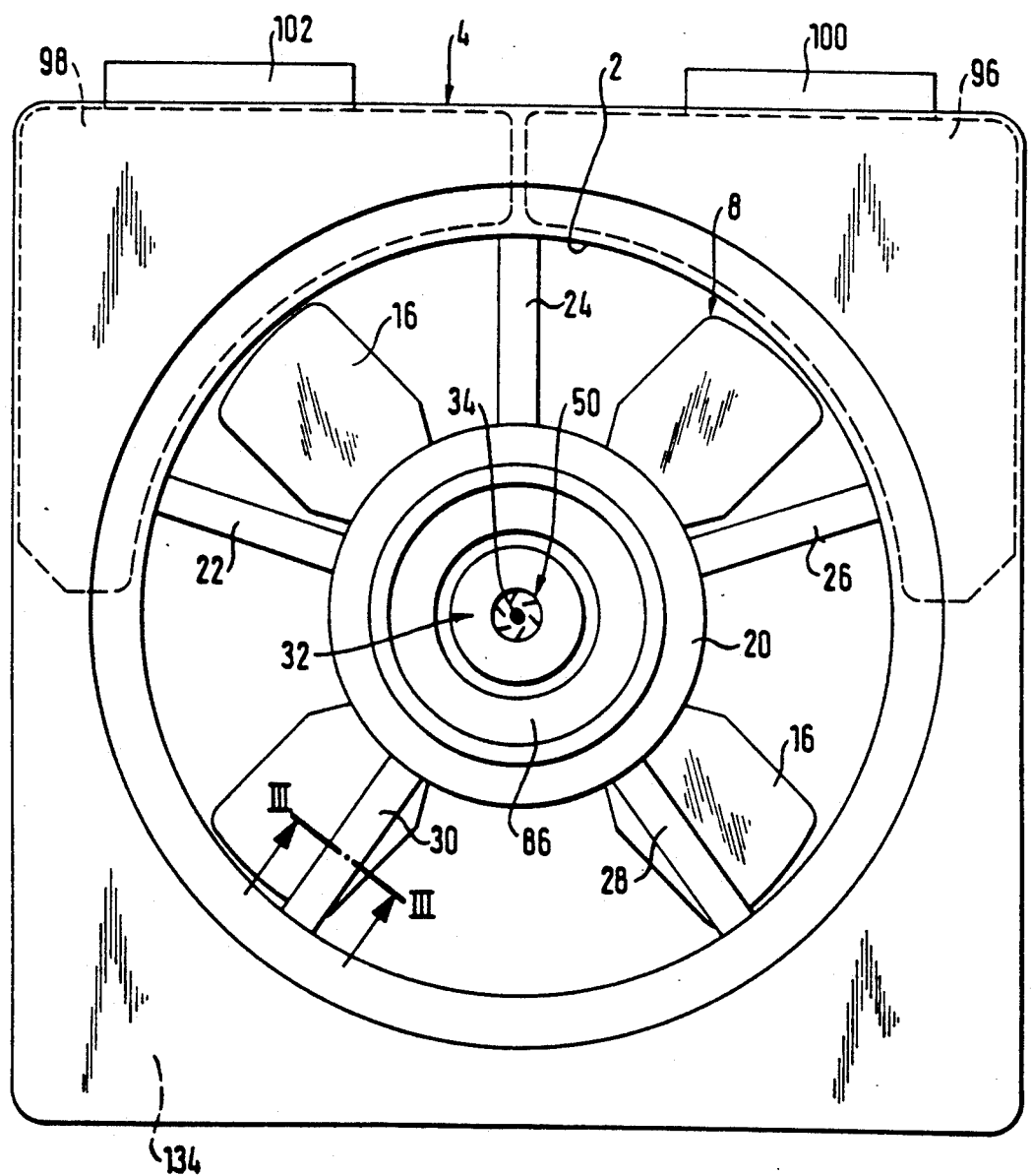
FIG. 2 shows a view of the apparatus according to FIG. 1 from the viewing direction II in FIG. 1.

As shown in FIG. 2, the tanks 96, 98 are arranged in a space 134 between the casing 4 and the air-ducting outer shell 2 at the top symmetrically with respect to the vertical longitudinal center plane of the casing 4. In this space 134 there is space at the bottom for electrical installations.

It will become apparent to those skilled in the art that various modifications and variations may be made to the apparatus of the invention without departing from the scope or spirit of the invention.

What is claimed is:

1. An apparatus for atomizing an active substance comprising:
    an air-ducting outer shell having in inlet section;
    a casing surrounding the air-ducting outer shell;
    a fan arranged in the inlet section of the air-ducting outer shell;
    an air-ducting inner shell arranged downstream of the fan;
    air-deflecting profiles extending between the air-ducting outer shell and the air-ducting inner shell;
    an atomizer arrangement surrounded by the air-ducting inner shell for atomizing active substance fed to it, which active substance emerges atomized from a downstream-directed active-substance outlet opening in the air-ducting inner shell; and
    a compressor, located in the air-ducting inner shell, which compressor sucks in air through an annular inlet surrounding the active-substance outlet opening and through an annular channel formed between the compressor and the air-ducting inner shell into its inlet opening facing the fan, and feeds the air compressed by it through its outlet opening, facing the active-substance outlet opening, to a swirling stream nozzle surrounding the active-substance outlet opening.

2. The apparatus as claimed in claim 1, wherein the swirling stream nozzle has a ring of deflecting surfaces which are inclined at equal angles with respect to radials, and which leave a central region free, and
    wherein the downstream edges of the deflecting surfaces are covered over radially on the outside by an annular surface.

3. The apparatus as claimed in claim 2, wherein the deflecting surfaces are plane.

4. The apparatus as claimed in claim 2, wherein the deflecting surfaces are curved.

5. The apparatus as claimed in claim 2, wherein there is placed against the upstream edges of the swirling stream nozzle a body of an active-substance feed nozzle, which has an active-substance outlet nipple protruding into the central region of the swirling stream nozzle.

6. The apparatus as claimed in claim 5, wherein there is coupled to the active-substance feed nozzle an ultrasonic generator, which sets the active-substance feed nozzle into axial oscillations, and wherein the outlet end of the active-substance outlet nipple of the active-substance feed nozzle is surrounded by a radial flange.

7. The apparatus as claimed in claim 6, wherein the ultrasonic generator includes an annular piezoelectric exciter fitted between a retaining flange of the active-substance feed nozzle and an active-substance inlet of the active-substance feed nozzle.

8. The apparatus as claimed in claim 7, wherein there is placed against the side of the piezoelectric exciter facing the active-substance inlet an annular block which has a substantially greater mass than the part of the active-substance feed nozzle lying downstream of the retaining flange.

9. The apparatus as claimed in claim 6 wherein at least one of the air-deflecting profiles is hollow and surrounds electrical lines to the compressor and to the ultrasonic generator.

10. The apparatus as claimed in claim 9 wherein feed lines lead from a rinsing-agent tank, an active-substance tank in the casing and from an outer third tank, and are connected through a common feed line containing a pump, to the active-substance feed nozzle.

11. The apparatus as claimed in claim 10, wherein the active-substance tank is connected to a circulating line, containing a second pump.

12. The apparatus as claimed in claim 10, wherein there are located in the feed lines solenoid valves which can be controlled by a program-control and a yes/no flowmeter in the common feed line.

13. The apparatus as claimed in claim 1 wherein the annular inlet is covered over by an annular filter.

14. An apparatus as claimed in claim 1, wherein a pair of tanks are respectively arranged in a space between the casing and the air-ducting outer shell at the top symmetrically with respect to a vertical longitudinal center plane of the casing, and wherein electrical installations are provided in this space at the bottom.

15. An apparatus as claimed in claim further comprising the combination of a swirling stream atomizer and an ultrasonic atomizer.

* * * * *